United States Patent [19]

Cornu et al.

[11] Patent Number: 4,579,845
[45] Date of Patent: Apr. 1, 1986

[54] ANTIHYPERTENSIVE CYANOGUANIDINES

[75] Inventors: Pierre-Jean Cornu, Paris; Claude Perrin, Orsay; Bernard Dumaitre, Bobigny; Gilles Streichenberger, Neuilly, all of France

[73] Assignee: Bouchara S.A., Paris, France

[21] Appl. No.: 565,030

[22] Filed: Dec. 8, 1983

[63] Continuation of PCT application PCT FR83/00066, Apr. 8, 1983.

[30] Foreign Application Priority Data

Apr. 8, 1982 [FR] France ................. 82 06128

[51] Int. Cl.⁴ ............... A61K 31/55; C07D 405/06
[52] U.S. Cl. ................. 514/212; 514/222; 514/237; 514/253; 514/256; 514/316; 514/321; 260/244.4; 544/58.6; 544/62; 544/129; 544/130; 544/333; 544/335; 544/364; 546/187; 546/197
[58] Field of Search ............... 546/197, 187; 544/129, 544/130, 333, 335, 364, 58.6, 62; 424/267, 246, 250, 251, 248.56; 260/244.4; 514/212, 316, 321, 237, 253, 222, 256

[56] References Cited

U.S. PATENT DOCUMENTS 3,006,913  10/1961  Mull ........................ 546/246 X
3,950,333  4/1976  Durant et al. ............... 548/242 X

OTHER PUBLICATIONS

*Chemical Abstracts*, 93: 106809f (1980) [Archibald, J., et al., *J. Med. Chem.*, 1980, 23(8), 857–61].

Primary Examiner—Richard A. Schwartz
Attorney, Agent, or Firm—Omri M. Behr

[57] ABSTRACT

This invention relates to novel tri-substituted guanidines linked to a piperidine ring.

More specifically, it relates to cyanoguanidines of formula I

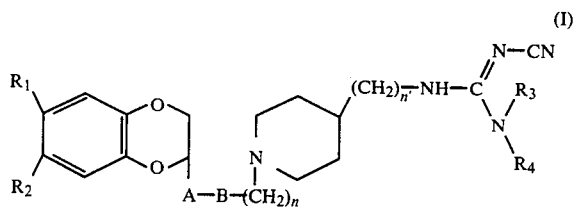

wherein
$R_1$, $R_2$, $R_3$, $R_4$ are substituents
n is an integer of zero to 1
n' is an integer of zero to 1
A and B are $-CH_2-$, CHOH, $-CO-$ or a single bond
as well as the acid addition salts thereof with a mineral or organic acid.

The compounds have interesting pharmacological properties which make them useful as active ingredient of medicines, e.g. antihypertensives.

11 Claims, No Drawings

ANTIHYPERTENSIVE CYANOGUANIDINES

This application is a continuation of PCT application PCT/FR83/00066, deposited Apr. 8, 1983.

This invention has for subject novel derivatives of guanidine as well as the processes for their manufacture.

It has more precisely as a subject the novel N-cyanoguanidines linked to a substituted piperidine ring.

Specifically it provides as a subject the [2,3-dihydrobenzo 1,4-dioxinyl-2]alkyl piperidinyl-4 (N-cyano N'-R)guanidines of the formula I

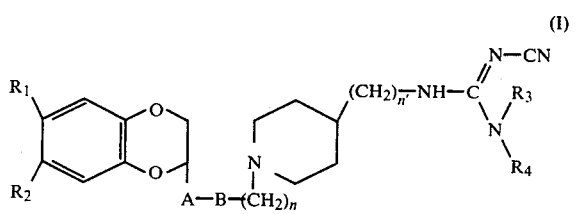

wherein $R_1$ and $R_2$, the same or different, represent hydrogen, a lower alkyl radical, a lower alkoxy radical, a halogen or a trifluoromethyl radical $R_3$ represents a lower alkyl radical, a lower alkenyl-radical, a lower cycloalkyl radical or a heterocyclanyl radical having 5, 6 or 7 bonds $R_4$ is a hydrogen, a lower alkyl radical, or the acyl residue of an organic carboxylic acid or $R_3$ and $R_4$ together form the alkylene moiety of a nitrogenous heterocycle optionally including an extra heteroatom n is an integer of 0 or 1 n' is an integer of 0 to 1

A is —CH$_2$— or a simple bond and B is —CHOH— or —CO— or A is —CHOH— or —CO— and B is a simple bond or —CH$_2$—

The formula I represents one of the possible structures of the cyanoguanidines. In acidic medium one of the nitrogen atoms of the guanidine function may be protonated. The result is that the compounds according to this invention may exist under one of the tautomeric forms (imino cyanoamine) and (amino-cyanoimine).

Moreover, the cyanogroup may be located on one or the other side of the plane defined by the double bond —C=N. The result is the possibility of an isomery syn and anti.

The tautomeric and isomeric forms are part of this invention.

This invention also provides the acid addition salt of the compounds of formula I with a mineral or organic acid, preferably with a therapeutically-compatible acid.

This invention still relates to the optically-active forms of the compounds of formula I as well as the diastereoisomeric forms of the compound of formula I.

Among the acid addition salts of the compounds of formula I, it may more particularly cited the hydrochlorides, the hydrobromides, the sulphates, the nitrates, the phosphates, the thiosulphates, the formates, acetates, maleates, fumarates, benzoates, 2,6-dichlorobenzoates, citrates, tartarates, (methoxy salicylates), 3,4,5-trimethoxybenzoates, vanillates, O-carbethoxy syringoates, naphtoates, benzene sulphonates, methylsulphonates, isethionates, nicotinates, isonicotinates, embonates and glucose-phosphates.

As far as the invention is concerned, a lower alkyl radical is a hydrocarbon chain having from 1 to 6 carbon atoms in the chain, in a straight or branched chain as for example methyl, ethyl, isopropyl, sec-butyl, tert-butyl, pentyl, neo-pentyl and n-hexyl.

A lower alkoxyradical has from 1 to 6 carbon atoms in the carbon chain which may be straight or branched as a methoxy, ethoxy, iso-propoxy, tertbutoxy or a pentyloxy.

An acyl radical derives from an organic carboxylic acid having from 1 to 12 carbon atoms as for example an alkyl carboxylic acid, an arylcarboxylic acid, an arylalkylcarboxylic acid, a cycloalkylcarboxylic acid or a heteroaryl carboxylic acid. It may be cited in this respect an acetyl radical, a butyroyl radical, a benzoyl radical, a 3,4,5-trimethoxy benzoyl radical, a cyclopropyl carbonyl radical or a nicotinoyl radical.

The meanings of the integers n and n' are of significance and play a definite role in the pharmacological properties of the compounds of formula I. The intensity or the duration of the effects of the compounds according to this invention may be modulated modifying the length of the hydrocarbon chain of one or the other part of the molecule.

When $R_3$ and $R_4$ together form the alkylene chain of a nitrogenous heterocycle, they represent with the nitrogen atom to which they are bound, a piperidinyl ring, a pyrrolidinyl ring, a hexamethylene imino ring, or a heptamethylene imino ring. When they incorporate an extra heteroatom, they represent a hexahydropyrimidyl ring, a tetrahydrothiazinyl ring, a morpholyl, a piperazinyl, a N-alkyl piperazinyl ring, a N-(hydroxyalkyl)-piperazinyl ring, a N-(alkoxyalkyl)piperazinyl ring or a N-(acyloxyalkyl)piperazinyl ring.

Among the compounds according to this invention, it may more specifically cited:

the compounds of formula $I_A$

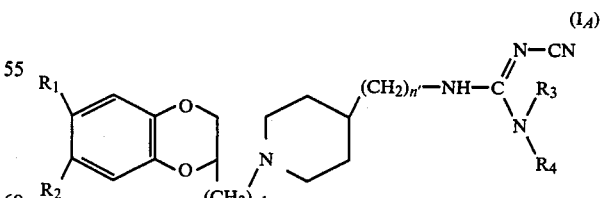

in which $n_1$ is an integer from 0 to 3 and $R_1$, $R_2$, $R_3$, $R_4$ and n' have the above-given meanings as well as the acid addition of the compounds of formula $I_A$ with a mineral or organic acid.

the compounds of formula $I_B$

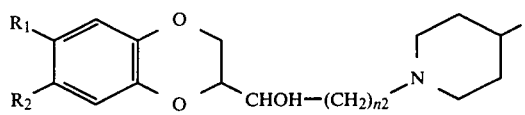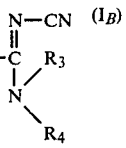

wherein
 $n_2$ is an integer from 0 to 2 and
 the substituents $R_1$, $R_2$, $R_3$, $R_4$ and $n'$ have the above-given meanings
as well as the acid addition salts thereof with a mineral or organic acid
 the compounds of formula $I_C$

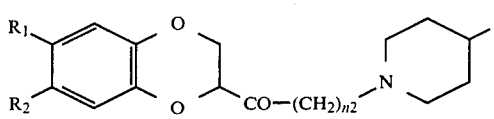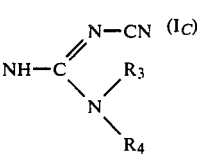

wherein $R_1$, $R_2$, $R_3$, $R_4$, $n'$ and $n_2$ have the above-given meanings as well as the acid addition salts thereof with a mineral or organic acid.

It may also be specifically cited the following compounds:
1-[2,3-dihydro[4H](1,4-benzodioxin-2 yl)methyl]4-(N-cyano-N'-methyl guanidinyl)piperidine
1-[2,3-dihydro[4H](1,4-benzodioxin-2 yl)methyl]4-[(N-cyano N'-methyl)guanidinyl methyl]piperidine
1-[2,3-dihydro[4H](1,4-benzodioxin-2 yl)methyl]4-[(N-cyano N'-allyl)guanidinyl methyl]piperidine
1-[2,3-dihydro[4H](1,4-benzodioxin-2 yl)methyl]4-[(N-cyano N'-(1-methyl propyl)guanidinyl methyl]piperidine
1-[2,3-dihydro[4H](1,4-benzodioxin-2 yl)methyl]4-[(N-cyano N'-cyclopropyl)guanidinyl methyl]piperidine These compounds according to the invention may be distinguished by their interesting pharmacological properties and namely by their anti-hypertensive and vaso-dilating properties correlated to a depressive action on the central nervous system.

Due to their high level of efficiency, the compounds of formula I or the acid addition salts thereof, find a use in human or veterinary therapy as active ingredients of the medicines intended to counteract or reduce the effects of the hypertensive condition.

For these purposes they are utilized in the form of pharmaceutical compositions designed for the administration by the parenteral, oral, rectal or sublingual ways.

According to this invention the pharmaceutical compositions include as active ingredient at least one compound of general formula I or an acid addition salt thereof with a mineral or organic acid, in conjunction or admixture with an inert non-toxic pharmaceutically-acceptable carrier.

As preferred forms of administration it may be cited the tablets or coated tablets, the capsules, the soft gelatine capsules, the multi-cores tablets, the drops, the drinkable solutions or suspensions; the injectable solutions or suspensions packed in ampoules, multidosis flasks or auto-injectable syringes; the suppositories; and the sublingual tablets.

The pharmaceutical compositions according to the invention may also include one or several other active ingredients of similar, complementary or synergistic action. It may thus be added either a diuretic agent of the thiazidic type such as cyclothiazide or of the triaminopteridine type such as triamterene or a β-blocking agent such as propranolol or pindolol.

The usual daily dosology may vary within broad limits as a function of the therapeutic use, the way of administration, the age of the patient and the oldness of the hypertensive illness. As a general rule, the dosology in the adult ranges from 0.1 to 50 mg per unitdosage and from 0.1 to 150 mg per day.

As a preferred feature, the pharmaceutical compositions according to the invention include from 0.1 to 25 mg of active ingredient per unit dosage.

This invention also provides a process for preparing the compounds of general formula I characterized in that a 4-aminopiperidine of general formula II

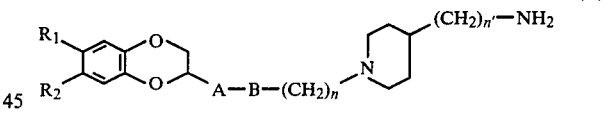

is reacted with a cyanoiminating reagent selected from the group consisting of
 alkyl cyanoimino isodithiocarbonates of general formula III

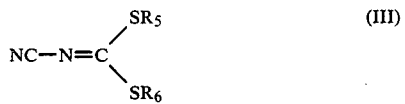

wherein $R_5$ and $R_6$ are a lower alkyl radical and alkyl mixed cyanoimino isothiocarbonates of general formula

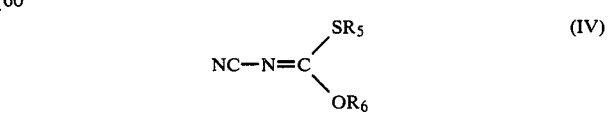

wherein $R_5$ and $R_6$ have the above-given meanings to produce an isothiourea or an isourea of general formula V

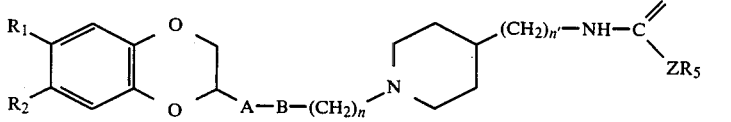

wherein the substituents $R_1$, $R_2$, $R_5$, n and n' are defined as above-given
and Z is an oxygen or a sulphur atom, which is condensed with a primary or a secundary amine of formula $R_3NHR_4$ to make the cyanoguanidine of general formula I

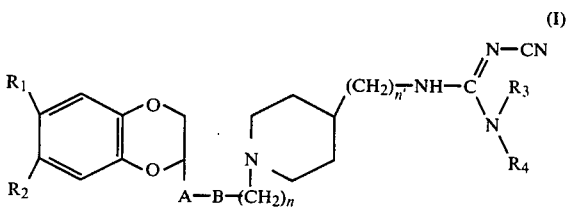

in which $R_1$, $R_2$, $R_3$, n and n' are defined as previously given and $R_4$ is a hydrogen or a lower alkyl radical which may if desired when $R_4$ is a hydrogen, be acylated by means of a functional derivative of a carboxylic acid to produce a N'-acyl N-cyanoguanidine of general formula I

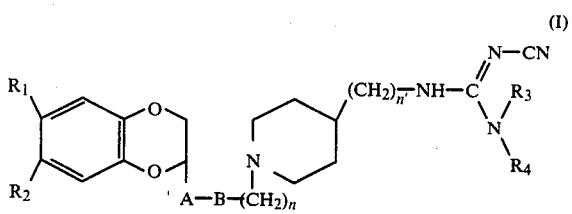

in which $R_1$, $R_2$, $R_3$, n and n' have the above-given meanings and $R_4$ is the acyl moiety of an organic acid having from 1 to 12 carbon atoms
or which may be resolved by means of an optically-active organic acid into its optical isomers
or which may be salified by adding a mineral or organic acid.

The starting 4-aminopiperidines of general formula II may be produced when n' is equal to zero by a process which consists in condensing a reactive ester of a benzodioxanyl alkyl or a benzodioxanyl hydroxy alkyl or a benzodioxanyl ketoalkyl with a blocked piperidone, making free the blocked ketonic function by hydrolysis, to obtain a 1-benzodioxanyl alkylpiperidin 4-one, condensing the latter with hydroxylamine or a salt thereof to get the corresponding oxime which is further reduced by means of a mixed hydride into an amine of formula II.

The reactive ester of benzodioxanyl alkyl is preferably a chloride, a bromide, an iodide, a methyl sulphonate or a p-toluene sulphonate.

The condensation with the piperidone is performed in a polar medium, preferably in the presence of an alkali metal iodide. The polar solvent is usually, pyridine, dimethylformamide, methyl ethylcetone or hexamethyl phosphorotriamide.

The alkali metal mixed hydride is a sodium or lithium aluminohydride, sodium borohydride, potassium borohydride, lithium trimethoxy borohydride or lithium cyanoborohydride.

The hydrolysis of the blocked piperidone is performed either by reacting with an aqueous mineral or organic acid or by exchange of functions with a ketoacid or with an aldehyde. The blocking may be obtained as a dialkyl ketal, as unsubstituted or substituted dioxolane or as a thioketal. As the hydrolysing means it may more conveniently be cited hydrochloric acid, sulphuric acid or p-toluene sulphonic acid.

In the general formula II wherein A or B is a CHOH or —CO— group the compounds are obtained from a benzodioxanyl alkyl ester of general formula III

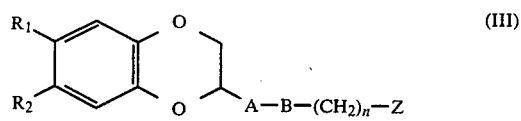

wherein
A or B represents a CHOH or CO grouping
Z in an easily-split acyl group
and n is equal to zero or one
which is condensed either with a blocked piperidone of general formula VI

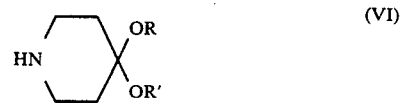

wherein R and R' are each a lower alkyl radical or together form a lower alkylene chain having from 2 to 4 carbon atoms. or with a piperidino 4-carboxamide of general formula VII

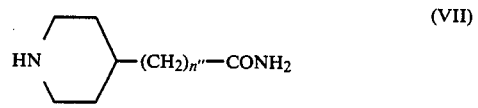

wherein n" is equal to 0 or 1
The resulting (benzodioxanyl alkyl)piperidine of general formula VIII

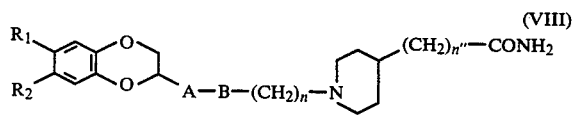

wherein
$R_1$ and $R_2$ have the above-given meanings
n is zero or one
n" is zero or one
is further reduced by means of an alkali metal mixed hydride into an amino derivative of general formula II

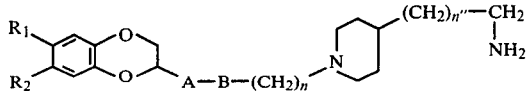

wherein the meanings of the several substituents remain inaltered which may be oxydized when A or B represent a hydroxy alkyl radical into a carbonyl group by means of a carbonylated derivative in the presence of aluminium isopropylate.

This invention further provides as means for the performance of the invention, the isothio- or iso ureas of general formula V

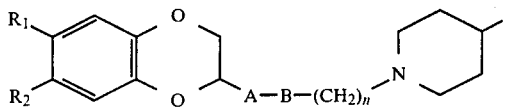 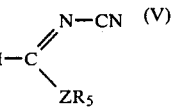

wherein the meanings of substituents A, B, $R_1$, $R_2$, $R_5$, n and n' remain those previously given and Z is an oxygen or a sulphur atom.

The following examples are merely intended for purpose of illustrating the invention. They do not limit it in any manner.

EXAMPLE 1

4-[2,3-dihydro[4H](1,4-benzodioxin-2 yl)methyl]1-(N-cyano N'-methylguanidinyl)piperidine

Step A

1-[(2,3-dihydro[4H]1,4-benzodioxin-2 yl)methyl]piperidone-4 ethyleneketal

A mixture of 184 g of 8-Aza 1,4-dioxasipro(4,5)decane, 320 g of 2-(methylsulphonyloxy methyl)1,4-benzodioxane and 180 g of potassium carbonate in 1500 ml toluene are heated to reflux under stirring for 17 hours. After this set of time the reaction mixture is washed with water then extracted with a N solution of hydrochloric acid. The hydrochloric solution is then made basic by adding diluted sodium hydroxide and extracted with ether. After drying and concentration, the desired product is obtained as a viscous oily residue weighing 328 g. The product is pure enough to be used as such for the next step of the synthesis.

Step B

1-[(2,3-dihydro[4H]1,4-benzodioxin-2 yl)methyl]piperidone-4

A mixture of 328 g of the oily residue of step A, 550 g concentrated hydrochloric acid and 3300 ml water are heated to reflux for 2 hours. After cooling the solution is extracted with ether then made basic by adding a concentrated solution of sodium hydroxide.

The alkaline medium is extracted with ether, washed with water, dried on sodium sulphate and concentrated. A solid compound is obtained which is recrystallized from Cyclohexane. 246 g of white crystals are thus recovered MP=95°-96°.

Step C

Oxime of 1-[(2,3-dihydro[4H]1,4-benzodioxin-2 yl)methyl]piperidone-4

72 g of 1-[(2,3-dihydro[4H](1,4-benzodioxin-2 yl)methyl]piperidone-4, 21 g of hydroxylamine hydrochloride are mixed together in a mixture of 80 ml water and 500 ml ethanol then heated to relfux for 30 mn.

After cooling, the hydrochloride of the desired oxime crystallises (MP=250°). The base is obtained from the latter by adding sodium hydroxide then extraction with chloroform. The chloroformic solution is dried and concentrated to dryness and 65 g of desired oxime are recovered (MP=115°).

Step D

1-[(2,3-dihydro[4H]1,4-benzodioxin-2 yl)methyl]4-amino piperidine 10 g of lithium aluminohydride are suspended in 150 ml anhydrous tetrahydrofuran and to this under stirring at room temperature a solution of 5 g of the oxime of 1-[(2,3-dihydro[4H]1,4-benzodioxin-2 yl)methyl]piperidone-4 in 300 parts of anhydrous tetrahydrofuran are dropwise poured.

The reaction mixture is then heated at 80° for 16 hours then cooled in an ice-bath. The excess of hydride is hydrolysed by adding some water.

After filtration of the precipitate of alumina on celite and concentration to dryness, the resulting oily residue is redissolved in ether. The ethereous phase is dried on sodium sulphate then concentrated to dryness. 35 g of the desired amino compound are recovered as an oil which may be used as such for the further step of the synthesis.

Step E

1-[(2,3-dihydro[4H]1,4-benzodioxin-2 yl)methyl]4-(N-cyano S-methylisothioureido)piperidine 7.2 g of 1-[(2,3-dihydro[4H]1,4-benzodioxin-2 yl)methyl]4-amino piperidine are mixed with 4.2 g of dimethyl cyanoimino dithiocarbonate and 100 ml ethanol then heated to reflux for 2 hours. After cooling, crystallization of a product takes place. It is filtered and washed with ethanol. 6.1 g of the desired product are thus obtained. It is purified for analysis and recrystallized from methanol. MP=168°.

Dimethyl cyanoimino dithiocarbonate is obtained according to the method described by R. J. Timmons and L. S. Wittenbrook—J. Org. Chem. 32 (1966) 1566.

It may be used under the same experimental conditions dimethyl mixed cyanoiminothiocarbonate obtained according to the technique described in the French Pat. No. 2,445,322. Accordingly 1-[(2,3-dihydro[4H]1,4-benzodioxin-2 yl)methyl]4-(N-cyano O-methyl isoureido)piperidine is produced.

Step F

1-[(2,3-dihydro[4H]1,4-benzodioxin-2 yl)methyl]4-(N-cyano N'-methyl guanidino)piperidine 10 g of 1-[(2,3-dihydro[4H]1,4-benzodioxin-2 yl)methyl]4-(N-cyano S-methyl isothioureido)guanidine are suspended in 200 ml methanol while maintaining the inner temperature to about 25° a stream of gazeous methylamine is bubbled until an absorption of 40 g takes place. The progression of the reaction is followed through TLC using the system toluene: 95—isopropylamine: 5.

After about 3 hours, the reaction is achieved and the mixture is concentrated to dryness. An oily product which crystallized by trituration with water, is obtained.

The thus obtained crystals are purified by recrystallizing them from isopropanol. 8 g of the desired cyanoguanidine which retains ½ mol of water of crystallization, is obtained.

MP=140°–142°.

EXAMPLE 2

1-[(2,3-dihydro[4H]1,4-benzodioxin-2 yl)methyl]4-[(N-cyano N'-cyano N'-methyl)guanidinyl methyl]piperidine

Step A

1-[(2,3-dihydro[4H]1,4-benzodioxin-2 yl)methyl]piperidine-4 carboxamide

A mixture of 245 g of 2-(tosyloxymethyl)benzodioxan, 130 g piperidine-4 carboxamide, 140 g potassium carbonate in 2000 ml xylene are heated to reflux for 3 hours under strong stirring.

The mixture which becomes gelatinous is further treated with stirring in heterogenous phase with 2 liters water. The thus formed solid is filtered, copiously washed with water then with isopropyl water. 190 g of the desired product are thus recovered as colourless crystals melting at 135°–136°, pure enough for the further step of the synthesis.

Step B

1-[(2,3-dihydro[4H]1,4 benzodioxin-2 yl)methyl]4-aminomethyl piperidine

To a suspension of 75 g of lithium aluminohydride in 500 ml tetrahydrofuran, a solution of 190 g 1-[(2,3-dihydro[4H]1,4 benzodioxin-2 yl)methyl]piperidine 4-carboxamide in 1500 ml tetrahydrofuran is added at room temperature under stirring. Once the addition achieved, the whole mixture is heated to the reflux of the solvent for 2 hours.

Excess of lithium aluminohydride is then hydrolysed by adding water under cooling. The solution is further filtered on celite and the filtrate concentrated to dryness. The oily residue is dissolved in ether and the resulting solution dried on anhydrous sodium sulphate.

After concentration to dryness, 124 g of the desired amine is recovered as a viscous oil.

The compound is pure enough to be used as such for the further steps of the synthesis.

Step C

1-[(2,3-dihydro[4H]1,4-benzodioxin-2 yl)methyl]4-[(N-cyano S-methyl isothioureido)methyl]piperidine 65.5 g of 1-[(2,3-dihydro[4H]1,4-benzodioxin-2 yl)methyl]4-aminomethyl piperidine are mixed with 36.5 g of dimethyl cyanoiminodithiocarbonate and 500 ml ethanol then heated to reflux for 4 hours.

By cooling the compound which crystallises is filtered, washed with ethanol and dried. 84 g isothiourea are obtained as colourless crystalls melting at 148°.

Step D

1-[(2,3-dihydro[4H]1,4-benzodioxin-2 yl)methyl]4-[(N-cyano N'-methyl guanidinyl)methyl]piperidine 10 g of 1[(2,3-dihydro[4H]1,4-benzodioxin-2 yl)methyl]4-[(N-cyano S-methylisothioureido)methyl]piperidine are suspended in 120 ml methanol and gazeous methylamine is bubbled while maintaining the temperature of the reaction mixture to about 30°.

The compound dissolves progressively and the bubbling is stopped when 50 g methylamine have been taken. The performance of the reaction may be following through TLC using the eluting mixture chloroform-isopropylamine as the solvent.

Usually after 2 hours bubbling, the reaction is achieved and the reaction mixture is evaporated to dryness. The resulting oily residue is washed with isopropyl ether.

After drying a brittle solid compound is obtained. It is not crystallized. The melting point is unclear, on about 100°.

EXAMPLE 3

1-[(2,3-dihydro[4H]1,4-benzodioxin-2 yl)methyl]4-[(N-cyano N'-(1-methyl propyl)guanidinyl methyl]piperidine A mixture of 3 g 1-[(2,3-dihydro[4H]1,4-benzodioxin-2-yl)methyl]4-[(N-cyano S-methyl isothioureido)methyl]piperidine obtained at step C of Example 2, 20 ml pyridine and 30 g allylamine are heated to the reflux for 16 hours.

The solution is then concentrated to dryness and taken up with isopropyl ether allowing the recovery of 6.5 g of colourless crystals melting at 136°–137°.

After recrystallization from isopropanol the melting point remains unaltered.

EXAMPLE 4

1-[(2,3-dihydro[4H]1,4-benzodioxin-2 yl)methyl]4-[N-cyano N'-(1-methyl propyl)guanidinyl methyl]piperidine A mixture of 3 g 1-[(2,3-dihydro[4H]1,4-benzodioxin-2-yl)methyl]4-[(N-cyano S-methyl isothioureido)methyl]piperidine, 10 ml pyridine and 30 g sec butylamine are heated to the reflux. After evaporation to dryness the resulting oily product is taken up in isopropyl ethyl allowing the recovery of a solid as colourless crystals. They are recrystallized from isopropanol.

The sec butylated derivative is obtained. 2 g. Melting point 145°.

EXAMPLE 5

1-[(2,3-dihydro[4H]1,4-benzodioxin-2 yl)methyl]4-[(N-cyano N'-propyl)guanidinyl methyl]piperidine A mixture of 4 g 1-[(2,3-dihydro[4H]1,4-benzodioxin-2-yl)methyl]4-[(N-cyano S-methyl isothioureido)methyl]piperidine, 15 ml pyridine and 30 g n-propylamine are heated to the reflux for 18 hours. After concentration to dryness, the so obtained oily residue is taken up in isopropyl ether giving rise to 3.5 g of a solid in the form of colourless crystals which are purified by recrystallization from isopropanol. Melting point 130°–131°.

EXAMPLE 6

1-[(2,3-dihydro[4H]1,4-benzodioxin-2 yl)methyl]4-[(N-cyano N'-cyclopropyl)guanidinyl methyl]piperidine A mixture of 6 g 1-[(2,3-dihydro[4H]1,4-benzodioxin-2-yl)methyl]4-[(N-cyano S-methyl isoureido)methyl]- piperidine, 20 ml pyridine and 30 g cyclopropylamine are similarly heated to reflux for 18 hours.

After concentration to dryness, the resulting oily residue is treated with isopropyl ether giving rise to the production of 5.4 g of colourless crystals which are recrystallized from ethanol. Melting point=162°

EXAMPLE 7

1-[(2,3-dihydro[4H]1,4-benzodioxin-2 yl)methyl]4-[(N-cyano N'-1,2,2-trimethyl propyl)guanidinyl methyl]piperidine 20 g 1-[(2,3-dihydro[4H]1,4-benzodioxin-2 yl)methyl]4-[(N-cyano S-methyl isothioureido)methyl]piperidine, 80 g, 3,3-dimethyl 2-butyl amine and 20 ml pyridine are mixed together and heated for 16 hours to reflux.

The mixture is concentrated to dryness. The resulting oily residue is washed several times with isopropyl ether. After drying under vacuum, the desired product is obtained as a vitreous solid compound which progressively melts at about 100°.

This compound is not crystallized but pure and shows through TLC only one spot using the mixture chloroform-isopropylamine (9:1) as the solvent

EXAMPLE 8

1-[(2,3-dihydro[4H]1,4-benzodioxin-2 yl)methyl]4-[(N-cyano N'-allyl)guanidinyl]piperidine Similarly a mixture of 10 g of 1-[(2,3-dihydro[4H]1,4-benzodioxin-2-yl)methyl]4-[(N-cyano S-methyl)isothioureido]piperidine and 60 ml allylamine is heated to reflux for 14 hours.

The solution is concentrated to dryness. The resulting oily residue is treated with isopropyl ether and gives colourless crystals. These crystals are washed with isopropyl ether, dried and recrystallized from isopropanol. 7.5 g of the allylated derivative are recovered as colourless crystals melting at 140°.

EXAMPLE 9

1-[(2,3-dihydro[4H]1,4-benzodioxin-2 yl)methyl]4-[(N-cyano N'-morpholino)guanidinyl methyl]piperidine A mixture of 5 g 1-[(2,3-dihydro[4H]1,4-benzodioxin-2-yl)methyl]4-[(N-cyano S-nethyl isothioureido)methyl]piperidine and 50 ml morpholine is heated to reflux for 20 hours.

The clear solution is then evaporated to dryness under reduced pressure. The resulting oily residue becomes solid by taking it up with ethyl ether.

The so obtained solid is filtrated, washed with ether, dried and recrystallized from acetonitrile after having it discolourized with animal charcoal.

1.3 g of the morpholino derivative are thus obtained, melting at 164°.

EXAMPLE 10

Pharmacological study of the compounds of formula I (a) acute toxicity

The mean lethal doses has been aproximately determined for the compounds of formula I by oral way in batches of 8 female mice (EOPS strain) from CESAL Breeding using the method of Campbell D. E. S. and Richter W. (Acta Pharmacol. and Toxicol 25, 1967, 345).

The treated animals have been kept under survey for 5 days. The mean lethal doses ($LD_{50}$) for the tested compounds range from 110 to 880 mg/kg per oral way.

(b) determination of a depressant action on the central nervous system

The compounds of formula I have been administered by oral way to batches of 5 female mice (EOPS strain) from CESAL Breeding at increasing doses from 5 to 50 mg/kg. The usual tests (traction chimney, escape, board with holes, temperature, ptosis, electroshock) have been performed one hour after the compound has been given.

The compounds induce a weak sedation with decrease of the body temperature, a slight ptosis and a decrease of the investigation behaviour.

(c) Determination of a vasodilating action

The peripheral vaso-dilating action of the compounds of formula I has been evidenced in the rats, namely at the level of hind paws. The vasodilating action induce at the same time an increase of the cutaneous temperature of the paws of 3° to 4°. This action arises depending on the compound at doses ranging from 1 to 5 mg/kg.

The vasodilating action joins a very significant inhibitory effect on the diuresis.

(d) Determination of the antihypertensive action

This test has been performed in hypertensive vigil male rats, the hypertension of which has been obtained by ligating the abdominal aorta. The compounds of formula I are administered by oral way at doses ranging from 2 to 10 mg/kg. They induce a decrease of the arterial pressure which is clear and protracted.

Moreover, the said compounds also cause a very significant hypotension when they are given in the anesthetized normo-tensive rats at a dose of 100 or 500 μg/kg.

EXAMPLE 11

1-[(6-methyl 2,3-dihydro[4H]1,4-benzodioxin-2 yl)methyl]4-[(N-cyano N'-allyl guanidinyl)methyl]piperidine Step A 2-hydroxymethyl 6-methyl 1,4-benzodioxan In a vessel fitted with a mechanical stirring device and a thermostatic device, 298 g 4-methyl pyrocatechol and 288 g epichlorhydrin are mixed then heated to 70°. A solution of 106 g sodium hydroxide in 800 ml water is then poured. The reaction is exothermic and the inner temperature increases up to about 80°–90°. The whole mixture is thereafter heated at 70° for 2,5 hours then poured into water. The resulting mixture is extracted with ethyl acetate. The organic phase is separated, washed with dilute sodium hydroxide then with saline water until the washings are neutral.

After drying and concentration, an oily residue is obtained which is distilled under vacuum and stream of nitrogen. The resulting 2-hydroxymethyl 6-methyl 1,4 benzodioxan is recovered as a viscous high-boiling oily compound (Eb P. under 0.2 mm 110° to 240°). The yield amounts to 188 g.

Step B 2-tosyloxymethyl 6-methyl 1,4-benzodioxan 188 g of 2-hydroxymethyl 6-methyl 1,4-benzodioxan obtained at step A are dissolved in 350 ml pyridine. The solution is cooled and then added to, portionwise, 199 g of p-toluene sulphonyl chloride while keeping the inner temperature to 20°–25°. The mixture is stirred for 18 hours at room temperature then poured into water and extracted with chloroform.

The chloroformic solutions are separated, washed with dilute hydrochloric acid then with saline water, dried and evaporated up. An orange oil is thus recovered. This oil is redissolved in 1000 ml warm isopropyl ether. By cooling the tosyl ester crystallizes. After filtration of the crystalls and drying 204 g of the tosyl ester are obtained as a solid compound melting at 84°–86°.

Step C

1-[(6-methyl 1,4-benzodioxan-2 yl)methyl]piperidino-4-carboxamide

A mixture of 167 g of the tosyl ester of step B, 64 g piperidino 4-carboxamide, 69 g potassium carbonate in 1000 ml xylene is heated to the reflux under stirring for 7 hours. After return to room temperature the mixture is washed with water and filtered. The solid residue is separated, washed many times with water then with isopropyl ether and dried.

82 g of the desired piperidino carboxamide are obtained as a colourless solid which melts at 138°.

Step D

1-[(6-methyl 1,4-benzodioxan-2 yl)methyl]4-aminomethyl piperidine 30 g of lithium aluminohydride are suspended under stirring in 750 ml tetrahydrofuran and to the suspension a solution of 88 g of the carboxamide of step C in 400 ml tetrahydrofuran is added thereto slowly at room temperature.

The mixture is thereafter heated to reflux for 3 hours. Excess of lithium aluminohydride is then hydrolysed by slow addition of water while cooling.

After filtration of the precipitate of alumina on Celite, the organic solution is concentrated to dryness. The resulting amine is recovered as an oil, homogeneous by TLC. The yield amounts to 59 g.

Step E

1-[(6-methyl 2,3-dihydro[4H]1,4-benzodioxin-2 yl)methyl]4-(N-cyano S-methyl isothioureido methyl)piperidine A mixture of 58.1 g 1-[(6-methyl 1,4-benzodioxan-2 yl)methyl]4-aminomethyl piperidine, 30.9 g dimethyl cyanoimino dithiocarbonate in 400 ml ethanol is heated to the reflux for 4 hours.

After cooling and storage for a night, the desired compound crystallizes. The crystals are filtered, washed with ethanol and dried. 54 g of the S-methyl isothiourea are recovered as colourless crystals melting at 145°.

Step F

1-[(6-methyl 2,3-dihydro[4H]1,4-benzodioxin-2 yl)methyl]4-[(N-cyano N'-allyl)guanidinyl methyl]piperidine 15 g of 1-[(6-methyl 2,3-dihydro[4H]1,4-benzodioxin-2 yl)methyl]4-(N-cyano S-methyl isothioureidomethyl)-piperidine is mixed with 30 ml pyridine and 70 ml allylamine. The resulting solution is heated to the reflux for 16 hours then evaporated off. An oily residue is recovered and ground with isopropyl ether until it crystallizes.

The resulting solid compound is purified by recrystallizing it from isopropanol, allowing the recovery of 11 g of the desired compound as a solid melting at 118°.

EXAMPLE 12

1-[6-methyl 2,3-dihydro[4H]1,4-benzodioxin-2 yl)methyl]4-[(N-cyano N'-methyl)guanidinyl methyl]piperidine 15 g of 1-[(6-methyl 2,3-dihydro[4H]1,4-benzodioxin-2 yl)methyl]4-[N-cyano S-methyl isothioureido methyl]piperidine obtained as described in Example 11 Step E, are suspended under stirring in 200 ml methanol and gazeous methylamine is bubbled therein while maintaining the inner temperature at about 25°.

The suspension progressively dissolves and when the solution is complete, the amount of absorbed methylamine is about 80 g.

The solution is kept under stirring for 18 further hours at room temperature then concentrated to dryness. The resulting oily residue crystallizes by trituration with ether.

The crystalline product is further purified by recrystallizing it from isopropanol.

9.8 g of colourless crystals are obtained which melts at 130°.

EXAMPLE 13

1[2-(2,3-dihydro[4H]1,4-benzodioxin-2 yl)ethyl]4-[(N-cyano N'-allyl)guanidinyl methyl]piperidine

Step A 3,4-dibromo butane nitrile

In a reactor fitted with a strong stirring device, 356 ml of allyl cyanide (i.e. 295 g) and 1,400 ml petroleum benzin (Eb 30°–40°) are mixed. The solution is cooled to −15° C. and 228 ml bromine (i.e. 704 g d=3.12) are added thereto dropwise while keeping the inner temperature at about the same level. The resulting 3.4-dibromo derivative separates. By decantation 480 ml of this compound is obtained which used as such immediately for the next step of the synthesis.

Step B 2-cyanomethyl 1,4-benzodioxan 440 g pyrocatechol dissolved in 3200 ml anhydrous acetone and 114 g potassium carbonate are suspended under vigourous stirring in a reactor. The whole mixture is heated to the reflux of the solvent and 30 ml of the 3,4-dibromo nitrile of step A are poured. Once this addition achieved 114 g potassium carbonate are anew added then once more 30 ml of the dibromo nitule of Step A. The same addition is renewed 16 times that means that in the whole 480 ml 3,4-dibromobutane nitrile and 1824 g potassium carbonate are added thereto.

The mixture is heated at the reflux for 20 hours. After reversion to room temperature, the thus resulting potassium bromide is separated by filtration and washed with acetone. The acetonic solutions are concentrated under reduced pressure up to dryness. The dry residue is washed with water and extracted with ether. The ethereous phase is washed with dilute sodium hydroxide then with saline water until the washings are neutral. After drying of the organic solution and evaporation to dryness, a dark yellow oil is obtained. This oil is purified by distillating it under vacuum allowing the recovery of 557 g of a clear oil which crystallises (Eb under 0.1 = 120°–123°).

The resulting benzodioxan may be recrystallized by dissolving it in 250 ml hot isopropanol and making it crystallized under stirring. A crystalline cake is thus obtained. The crystalls are ground, dried and washed petroleum benzin (Eb 30°–40°). 538 g of pure 2-cyanomethyl 1,4-benzodioxan are produced melting at 66°–67°.

Step C (1,4-benzodioxan-2yl)acetic acid

A mixture of 175 g 2-cyanomethyl 1,4-benzodioxan, 250 ml water, 250 ml acetic acid and 100 ml concentrated sulphuric acid are heated to reflux for 48 hours. The reaction mixture is then poured in 5000 ml water and the whole is kept under stirring. The thus found crystalls are filtered, washed with water and dried, giving rise to 172 g (1,4-benzodioxan-2yl)acetic acid melting at 95°.

Step D 2-(1-hydroxyethyl) 1,4-benzodioxan

In a flask fitted with a stirrer and a condenser, a suspension of 50 g lithium aluminohydride in 1500 ml tetrahydrofuran is introduced. A solution of 172 g of the acid formed at step C in 500 ml tetrahydrofuran is added thereto dropwise.

Once the addition achieved, the whole is boiled for 18 hours. After return to room temperature the excess of reagent is destroyed by adding water in the cold dropwise, then the precipitate of alumina is filtered on celite.

The solution is thereafter concentrated to dryness taken up with 1000 ml ethanol, filtered and anew concentrated to dryness.

The resulting oily residue is distilled under reduced pressure and 132 g of the pure hydroxylated derivative is obtained as a viscous colourless oil (Eb under 0.05 = 119°–122°).

Step E 2-(1-tosyloxyethyl) 1,4-benzodioxan 132 g of the hydroxylated derivative of step D is dissolved in 260 ml pyridine and the solution is cooled to 5°–10°. To this 139.4 g p-toluene sulphonyl chloride are added portionwise while maintaining the temperature to this level. After 4 hours stirring at room temperature, the mixture is poured into 4000 ml water and the suspension is extracted with methylene chloride. The methylenic solution is washed with hydrochloric acid then with saline water.

After drying of the organic phase and distillation, a yellow oil is recovered which is redissolved in the hot in 800 ml ethanol. By cooling the solution crystallizes. The crystals are filtered, washed and dried. 75 g of the desired tosyloxy derivative are obtained which melts at 95°.

Step F

1-[1-(1,4-benzodioxan-2 yl)ethyl]piperidine-4 carboxamide

A mixture of 104 g of tosyloxy derivative of step E, 40 g piperidine-4 carboxamide and 43 g potassium carbonate suspended in 750 ml xylene are heated for 7 hours to the reflux under stirring.

After return to ambient temperature, the mixture is taken up with water under stirring and filtered. The resulting solid is separated, washed many times with water then with isopropyl ether.

The compound is dried and 78 g of this are recovered, melting at 190°. This compound may be used as such for the next step of the synthesis.

Step G

1-[1-(1,4-benzodioxan-2 yl)ethyl]4-aminomethyl piperidine

In a suspension of 30 g lithium aluminohydride in 1000 ml tetrahydrofuran 78 g of the carboxamide of step F as the solid is added thereto portionwise.

The temperature remains at about 35°–45°. After completion of the addition the mixture is heated for 3 hours to the reflux.

The excess of lithium aluminohydride is destroyed by slow addition of water while cooling. After filtration on celite, the solution is concentrated to dryness giving rise to the recovery of an oily residue which is taken up in ether. The ethereous solution is dried on sodium sulphate and concentrated to dryness under vacuum. The desired aminated derivative is obtained as a yellow oil, pure on VPC. The yield amounts to 73 g.

Step H

1-[1-(2,3-dihydro[4H]1,4-benzodioxin-2 yl)ethyl]4-[(N-cyano S-methy isothioureido)methyl]piperidine A mixture of 73 g of the aminated compound of step G and 38.6 g of dimethyl cyanoimino dithiocarbonate in 500 ml ethanol is heated for 4 hours to the reflux. After return to room temperature the compound crystallizes.

the crystals are filtered, washed with ethanol and dried under vaccuum, 85 g of 1-[1-(2,3-dihydro[4 H]1,4-benzodioxin-2 yl)ethyl]4-[(N-cyano S-methyl isothioureido)methyl]piperidine are obtained as colourless crystals showing a double melting point 145° then solidification and re-melting at 155°.

Step I

1-[1-(2,3-dihydro[4H]1,4-benzodioxin-2 yl)ethyl]4-[(N-cyano N'-allyl)guanidinyl methyl]piperidine A mixture containing 15 g 1-[1-(2,3-dihydro[4H]1,4-benzodioxin-2 yl)ethyl]4-(N-cyano S-methyl isothioureido)methyl piperidine of step H, 50 ml pyridine and 50 ml allylamine is boiled for 6 hours.

After evaporation to dryness a pasty residue is obtained which crystallizes by triturating it with isopropyl ether. The resulting crystals are filtered, washed and dried under vaccuum.

By recrystallization from isopropanol 14 g of the pure compound are produced melting at 131°.

* EXAMPLE 14

1-[1(2,3-dihydro[4H]1,4-benzodioxin-2 yl)ethyl]4-[(N-cyano N'-methyl)guanidinyl methyl]piperidine 15 g of 1-[1-(2,3-dihydro[4H]1,4 benzodioxin-2 yl)ethyl]4-[(N-cyano S-methyl isothioureido)methyl]piperidine produced at step H of Example 13 are suspended under stirring in 250 ml methanol then gazeous methylamine is bubbled thereto while keeping the inner temperature at about 25°–30°. The mixture dissolves progressively and the solution is clear when 120 g methylamine has been absorbed. The whole mixture is stirred for 18 hours at room temperature then evaporated to dryness. The pasty residue crystallizes by trituration with ether.

The crystals are purified by recrystallization from isopropanol giving rise to 11 g of the pure compound which melts at 125°. The compound appears as colourless crystals.

EXAMPLE 15

1-[1-(2,3-dihydro[4H]1,4-benzodioxin-2 yl)2-hydroxyethyl]4-[(N-cyano N'-allyl)guanidinyl methyl]piperidine

Step A

1-[1-(2,3-dihydro[4H]1,4-benzodioxin-2 yl)2-hydroxy ethyl]piperdine-4 carboxamide In a reactor fitted with a Dean-Stark separator and a stirring device 81 g of 2-[(1-bromo 2-hydroxy)ethyl]1,4 benzodioxan obtained according to J. Med. Chem. 13 (1970) 175, are mixed with 40 g piperidine 4-carboxamide, 40 g potassium carbonate and 750 ml xylene.

The whole mixture is heated to reflux for 7 hours under stirring. After return to room temperature the solid matters are filtered, washed many times with water then with isopropanol. 66 g of the desired compound are obtained as creamy-coloured crystals melting at 186°. The compound is pure enough to be used without further purification for the next step of the synthesis.

Step B

1-[1-(2,3-dihydro[4H]1,4-benzodioxin-2 yl)2-hydroxy ethyl]4-aminomethyl piperidine A suspension of 30 g lithium aluminohydride in 1000 ml tetrahydrofuran is prepared under stirring and at room temperature. To this suspension 66 g of previously ground 1-[1-(2,3-dihydro[4H]1,4-benzodioxin-2 yl)2-hydroxy ethyl]piperidine 4-carboxamide are added portionwise.

Once the addition achieved, the mixture is heated to reflux for 3 hours. The excess of lithium aluminohydride is thereafter destroyed by adding water while maintaining the temperature at 0°.

After filtration on celite, the resulting solution is concentrated to dryness under vaccuum producing 57 g of the aminomethyl derivative as a clear orange oil.

Step C

1-[1-(2,3-dihydro[4H]1,4-benzodioxin-2 yl)2-hydroxy ethyl]4-[(N-cyano S-methyl isothioureido)methyl]piperidine A mixture of 58 g 1-[1-(2,3-dihydro[4H]1,4-benzodioxin-2 yl)2-hydroxy ethyl]4-aminomethyl piperdine and 29 g dimethyl cyano imino dithiocarbonate in 400 ml ethanol, is heated for 4 hours to the reflux. The solution is then concentrated to dryness and the residue is taken up in isopropyl ether giving rise to the production of crystals which are filtered, washed with isopropyl ether and dried.

By recrystallization from isopropanol, 58 g of the isourea are obtained, melting at 128°.

Step D

1-[1-(2,3-dihydro[4H]1,4-benzodioxin-2 yl)2-hydroxyethyl]4-[(N-cyano N'-allyl)guanidinyl methyl]piperidine The mixture of 15.6 g of 1-[1-(2,3-dihydro[4H]1,4-benzodioxin-2 yl)2-hydroxy ethyl]4-[(N-cyano S-methyl isothioureido)methyl]piperidine, 50 ml pyridine and 70 ml allylamine is boiled for 16 hours.

After concentration to dryness a viscous oily residue is recovered which is crystallized by trituration with ether.

17.4 g of crystals are thus obtained which are purified by recrystallization from hot isopropanol then cooling.

1-[1-(2,3-dihydro[4H]1,4-benzodioxin-2 yl)2-hydroxy ethyl]4-[(N-cyano N'-allyl)guanidinyl methyl]piperidine appears as colourless crystals melting at 130°.

EXAMPLE 16

1-[1-(2,3-dihydro[4H]1,4-benzodioxin-2 yl)2-hydroxy ethyl]4-[(N-cyano N'-methyl)guanidinyl methyl]piperidine 15.6 g of 1-[1-(2,3-dihydro[4H]1,4-benzodioxin-2-yl)2-hydroxy ethyl]4-[(N-cyano S-methyl isothioureido)methyl]piperidine obtained as indicated at Example 15 step C, are suspended under stirring in 250 ml methanol and gazeous methylamine is bubbled thereto while maintaining the inner temperature at about 25°–30°. The bubbling is stopped when the dissolution is complete and then the amount of absorbed methylamine is about 80 g. The whole mixture is further stirred for 18 hours at room temperature, then evaporated to dryness giving rise to a viscous oil which is taken up in acetonitrile.

After few hours standing, crystallization initiates and the crystals are separated by filtration, washed and dried. 14.6 g of the desired guanidine are obtained and may be recrystallized from isopropanol. After recrystallization the pure compound melts at 150°.

What we claim is:

1. A compound selected from the group consisting of
(A) a 1-[(2,3-dihydrobenzo-1,4-dioxinyl-2)alkyl]4-[(N-cyano-N'-R)-guanidinyl]piperidine of the formula

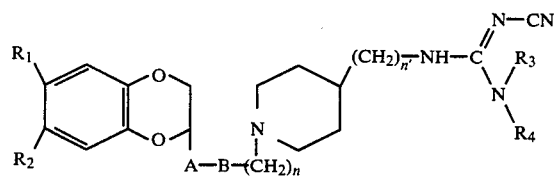

wherein
A is —CH$_2$ or a single bond and B is —CHOH or —CO— or A is —CHOH— or —CO— and B is a single bond or —CH$_2$—
R$_1$ and R$_2$ are the same or different and are hydrogen, a lower alkyl radical, a lower alkoxy radical, a halogen atom or a trifluoromethyl radical,
R$_3$ is a lower alkyl radical, a lower alkenyl radical, or a lower cycloalkyl radical,
R$_4$ is hydrogen, a lower alkyl radical or the acyl moiety of an organic carboxylic acid having up to 12 carbon atoms or R$_3$ and R$_4$ together with the nitrogen atom to which they are attached form a heterocycle selected from the group consisting of piperidino, pyrrolidino, hexamethylene imino, heptamethylene imino, hexahydropyrimidyl, tetrahydrothiazinyl, morpholino, piperazino, N-loweralkyl-piperazino, N-(hydroxyloweralkyl)piperiazino, N-(loweralkoxyloweralkyl)piperazino, wherein acyl is as defined as in R$_4$,
n is an integer of 0 or 1, and
n' is an integer of 0 or 1,
wherein the term "lower alk" means 1 to 6 carbon atoms and the term "cyclo alk" 3 to 6 carbon atoms,
(B) a 1-[(2,3-dihydrobenzo-1,4-dioxinyl-2)-alkyl-4-(N-cyano-N'-R-guanidinyl]-piperidine having the formula I$_A$

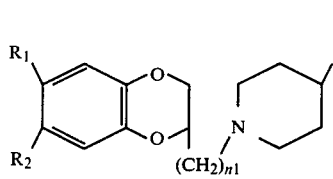
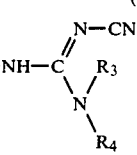

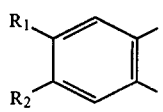
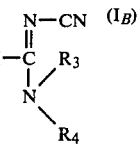

wherein the substituents

R₁R₂, R₃, R₄, and n' have the above-given meanings, and $n_1$ is an integer of 1 to 3; and (C) the therapeutically acceptable acid addition salts thereof with a mineral or an organic acid forming such salts.

2. An acid addition salt of a compound according to claim 1.

3. A compound selected from the group consisting of optically-active isomers of a compound of claim 2 and its diastereo isomers.

4. A compound selected from the group consisting of compounds according to claim 1 having the formula $1_A$

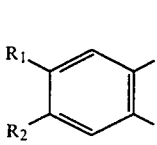

wherein the substituents

R₁, R₂, R₃, R₄ and n' have the meanings of claim 1, and $n_1$ is an integer of 1 to 3 and the therapeutically acceptable salts thereof with a mineral or an organic acid forming such salts.

5. A compound according to claim 1 selected from the group consisting of compounds having the formula $I_B$

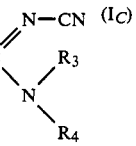

wherein the substituents

R₁, R₂, R₃, R₄ and n' have the definitions of claim 1, and $n_2$ is an inetger of 0 to 2, and the acid therapeutically acceptable addition salts thereof with a mineral or organic acid.

6. A compound according to claim 1 selected from the group consisting of compounds having the formula $I_C$

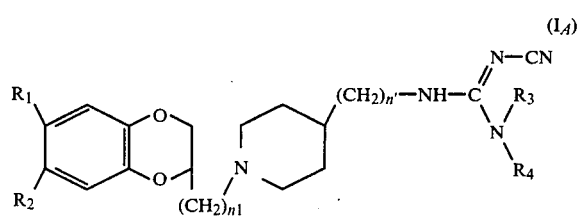

wherein the substituents

R₁, R₂, R₃, R₄ and n' have the meanings of claim 1, and $n_2$ is an integer of 0 to 2, and the therapeutically acceptable acid addition salts thereof with a mineral or organic acid.

7. 1-[(2,3-dihydro-[4H]-1,4-benzodioxin-2-yl)methyl]-4-(N-cyano-N'-methyl)-guanidinyl piperidine according to claim 1.

8. 1-[(2,3-dihydro-[4H]-1,4-benzodioxin-2-yl)methyl]-4-[(N-cyano-N'-methyl)-guanidinylmethyl]piperidine according to claim 1.

9. 1-[(2,3-dihydro-[4H]-1,4-benzodioxin-2-yl)methyl]-4-[(N-cyano-N'-allyl)-guanidinylmethyl]piperidine according to claim 1.

10. A pharmaceutical composition for treating hypertensive conditions containing as active ingredient from 0.1 to 50 mg of a compound of claim 1 in admixture or in conjunction with an inert non-toxic pharmaceutically-acceptable carrier or vehicle.

11. A pharmaceutical composition for treating hypertensive conditions according to claim 1 which further contains one or several active ingredients having similar, complementary or synergistic activity.

* * * * *